United States Patent [19]

Schnizer

[11] Patent Number: Plant 6,565

[45] Date of Patent: Jan. 31, 1989

[54] CHRYSANTHEMUM PLANT NAMED SCHNIZER'S TWILIGHT

[75] Inventor: William O. Schnizer, Waco, Tex.

[73] Assignee: Ball Pan Am Plant Co., Parrish, Fla.

[21] Appl. No.: 61,426

[22] Filed: Jun. 15, 1987

[51] Int. Cl.[4] ..... A01H 5/00

[52] U.S. Cl. ..... Plt./74

[58] Field of Search ..... Plt. 74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Schnizer's Twilight, distinguished from its parent cultivar Twilight by its dark coral bronze flower color.

1 Drawing Sheet

1

The present invention comprises a new and distinct cultivar of *Chrysanthemum morifolium,* Ramat., hereinafter referred to by the cultivar name Schnizer's Twilight.

The new cultivar is a sport of Twilight and was discovered by the inventor William O. Schnizer in Waco, Tex. growing in a bench of flowering plants of the parent cultivar. The new cultivar was immediately recognized by virtue of its salmon-bronze flower color, as opposed to the lavender pink flower color of Twilight.

The first act of asexual reproduction of Schnizer's Twilight was accomplished when vegetative cuttings were taken from the initial selection in February 1984 in a controlled environment in Waco, Tex. by William O. Schnizer. Horticultural examination of selected units initiated in February 1984 has demonstrated that the combination of characteristics as herein disclosed for Schnizer's Twilight are firmly fixed and are retained through successive generations of asexual reproduction.

The following traits have been repeatedly observed and are determined to be basic characteristics of Schnizer's Twilight, which in combination distinguish this Chrysanthemum as a new and distinct cultivar:

1. Daisy pot mum, flat capitulum form, single capitulum type.
2. Salmon bronze ray florets which fade as blooms mature.
3. Capitulum 45–65 mm across, ray florets 20–30 mm long and 12–15 wide at maturity, about 24 ray florets per capitulum.
4. Disc florets yellow when mature, light yellow-green immature.
5. Has the same properties and distinguishing characteristics as Twilight except for the flower color.

Schnizer's Twilight has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

Of the many commercial cultivars known to the present inventor, the most similar in comparison to Schnizer's Twilight is Twilight. Schnizer's Twilight has dark coral bronze ray florets whereas the parent Twilight has bright lavender-pink ray florets. All other characteristics are essentially the same.

The accompanying photographic drawing shows typical inflorescence and foliage characteristics of

2

Schnizer's Twilight. The photograph is in black and white, with four (4) flowers being colored to accurately depict true color. Two flowers show the darker color when opening and two show the color to which the flowers fade when maturing.

In the following description, color references are made to the Royal Horticultural Society Colour Chart. The color values were determined at approximately noon on Apr. 22, 1987 under fluorescent light at Parrish, Fla.

Classification:

*Botanical.*—*Chrysanthemum morifolium,* Ramat., cv. Schnizer's Twilight.

*Commercial.*—Daisy pot mum.

INFLORESCENCE

A. Capitulum:
- *Form.*—Flat.
- *Type.*—Single.
- *Diameter across face.*—45–65 mm.

B. Corolla of ray florets:
- *Color (general tonality from a distance of three meters).*—Dark coral bronze.
- *Color (upper surface).*—181A fading to 181C.
- *Color (under surface).*—179C.

C. Corolla of disc florets:
- *Color (mature).*—Yellow.
- *Color (immature).*—Lime green.

D. Reproductive organs:
- *Androecium.*—Present in disc florets only.
- *Gynoecium.*—Present in both disc and ray florets.

PLANT

A. General appearance:
- *Height.*—30–35 cm above the edge of the pot, the height varies depending upon growing conditions.

B. Foliage:
- *Color (upper surface).*—147A.
- *Color (under surface).*—147B.
- *Shape.*—Ovate with cleft margins.

I claim:

1. A new and distinct cultivar of Chrysanthemum plant named Schnizer's Twilight, as illustrated and described, and distinguished from its parent cultivar Twilight by its dark coral bronze flower color.

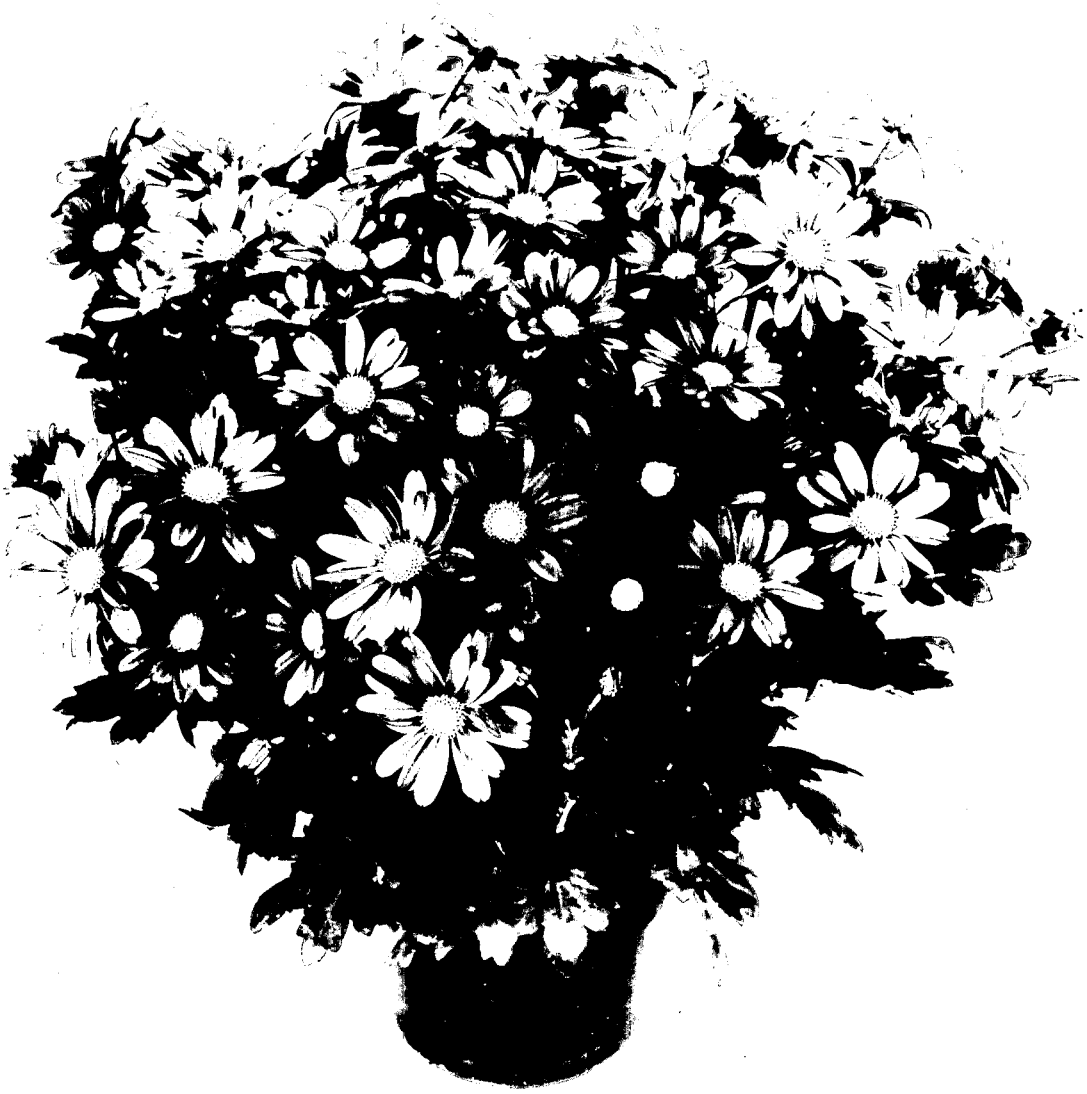

* * * * *